United States Patent [19]
Slayton et al.

[11] Patent Number: 6,050,943
[45] Date of Patent: Apr. 18, 2000

[54] IMAGING, THERAPY, AND TEMPERATURE MONITORING ULTRASONIC SYSTEM

[75] Inventors: Michael H. Slayton, Tempe; Peter G. Barthe, Phoenix, both of Ariz.

[73] Assignee: Guided Therapy Systems, Inc., Mesa, Ariz.

[21] Appl. No.: 08/950,353

[22] Filed: Oct. 14, 1997

[51] Int. Cl.[7] .................................................. A61B 8/00
[52] U.S. Cl. .............................................. 600/439; 601/3
[58] Field of Search ...................... 601/2, 3, 4; 600/439; 606/1; 604/22

[56] References Cited

U.S. PATENT DOCUMENTS

| | | | |
|---|---|---|---|
| 4,276,491 | 6/1981 | Daniel | 310/317 |
| 4,757,820 | 7/1988 | Itoh . | |
| 4,807,633 | 2/1989 | Fry . | |
| 5,209,720 | 5/1993 | Unger . | |
| 5,360,268 | 11/1994 | Hayashi et al. . | |
| 5,370,121 | 12/1994 | Reichenberger et al. . | |
| 5,435,311 | 7/1995 | Umemura et al. | 128/660.03 |
| 5,501,655 | 3/1996 | Rolt et al. | 601/3 |
| 5,522,869 | 6/1996 | Burdette et al. | 607/97 |
| 5,526,815 | 6/1996 | Granz et al. | 128/660.03 |
| 5,620,479 | 4/1997 | Diederich | 607/97 |
| 5,655,538 | 8/1997 | Lorraine et al. | 128/662.03 |
| 5,657,760 | 8/1997 | Ying et al. | 128/660.03 |
| 5,697,897 | 12/1997 | Buchholtz | 604/22 |
| 5,722,411 | 3/1998 | Suzuki et al. | 128/660.03 |
| 5,769,790 | 6/1998 | Watkins et al. | 600/439 |

OTHER PUBLICATIONS

Noninvasive Estimation of Tissue Temperature Response to Heating Fields Using Diagnostic Ultrasound, Ralf Seip and Emad S. Ebbini, IEEE Transactions on Biomedical Engineering, vol. 42, No. 8, Aug., 1995, pp.828–839.

*Transrectal Ablation of Prostate Tissue Using Focused Ultrasound*, N.T. Sanghvi, R.S Foster, R. Bihrle, F.J. Fry, M. Phillips and C. Hennige, 1993 Ultrasonics Symposium, pp. 1207–1210.

Non–Intrusive Measurement of Microwave and Ultrasound–Induced Hyperthermia by Acoustic Temperature Tomography, S. A. Johnson, Ph.D., D. A. Christansen, Ph.D., C. C. Johnson, Ph.D., J. F. Greenleaf, Ph.D. and B. Rajagopalan, Ph.D., 1977 Ultrasonics Symposium Proceedings,pp. 977–982.

An Acoustic Phase Shift Technique for the Non–Invasive Measurement of Temperature Changes in Tissues, Brian J. Davis and Padmakar P. Lele, 1985 Ultrasonics Symposium, pp. 921–924.

*Ultrasound Thermometry in Hyperthermia*, S. Ueno, M. Hashimoto, H. Fukukita and T. Yano, 1990 Ultrasonic Symposium, pp. 1645–1652.

*Human Cancer Treatment with Ultrasound*, Peter M. Corry, Khaled Jabboury, Elwood P. Armour and Joseph S. Kong,, IEEE Transactions on Sonics and Ultrasonics, vol. SU–31, No. 5, Sep., 1984, pp. 444–456.

*Primary Examiner*—Brian L. Casler
*Attorney, Agent, or Firm*—Snell & Wilmer, L.L.P.

[57] ABSTRACT

An ultrasonic system useful for providing imaging, therapy and temperature monitoring generally comprises an acoustic transducer assembly configured to enable the ultrasound system to perform the imaging, therapy and temperature monitoring functions. The acoustic transducer assembly comprises a single transducer that is operatively connected to an imaging subsystem, a therapy subsystem and a temperature monitoring subsystem. The ultrasound systems may also include a display for imaging and temperature monitoring functions. An exemplary single transducer is configured such that when connected to the subsystems, the imaging subsystem can generate all image of a treatment region on the display, the therapy subsystem can generate high power acoustic energy to heat the treatment region, and the temperature monitoring subsystem can map and monitor the temperature of the treatment region and display the temperature on the display, an through the use of the single transducer. Moreover, the acoustic transducer assembly is configured such that the imaging, therapeutic heating and temperature monitoring of the treatment region can be conducted substantially simultaneously.

19 Claims, 11 Drawing Sheets

ROI=REGION OF INTEREST

| VPP | 1.386 | [V] |
| --- | --- | --- |
| PW (-20dB) | 1.480 | [US] |
| TRIGGER DELAY | 25.040 | [US] |

| FC | 3.369 | [MHZ] |
| --- | --- | --- |
| FBW | 44.203 | [%] |
| FH | 4.114 | [MHZ] |
| FP | 3.040 | [MHZ] |
| FL | 2.625 | [MHZ] |

TYPE   5X5 mm THERAPY/IMAGING/MONITORING TRANSDUCER

IMAGING, THERAPY, AND TEMPERATURE MONITORING ULTRASONIC SYSTEM

BACKGROUND OF THE INVENTION

1. Field of the Invention

This invention generally relates to a non-invasive therapeutic ultrasonic system, and more particularly, to a system which is capable of acoustically imaging and heating a certain region to be treated ("the treatment region") in target tissue for therapeutic purposes as well as acoustically monitoring the temperature profile of the treatment region.

2. Description of the Related Art

The absorption of energy in tissue, for example, in the human body produces an increase in temperature, which can be exploited for therapeutic purposes. The irradiation of ultrasound to the target tissue such as in the human body, which has been successfully used for decades mainly in increasingly sophisticated diagnostic imaging applications, also allows the target tissue to absorb a certain amount of energy. Thus, ultrasound may be used in the therapeutic uses.

Specifically, ultrasonic energy at frequencies above 1.5 MHz has an acoustic wavelength less than 1 mm in the human tissue. This energy is easily controlled in beamwidth and depth of penetration, and has a favorable absorption characteristic in the tissue. These aspects allow the energy to be precisely localized such that regions may be selectively heated while sparing overlying tissue structures.

Ultrasound has significant advantages for therapeutic applications as compared to micro-wave radio-frequency (RF) energy or optical energy (laser light). In contrast with the ultrasound, the RF energy is characterized by long wavelengths in the tissue, with limited to poor control of energy deposition, and high absorption. These aspects of the RF energy constrain its therapeutic usage to large superficial areas. On the other hand, the optical energy which is typically emitted from lasers can be precisely controlled in beamwidth, but the opacity and high absorption in the tissue also limits its use to surface treatment or invasive procedures. Furthermore, the laser and RF energy are emitted from ionizing radiation sources which are typically associated with some risk, unlike acoustic transducers which are typically used for generating ultrasound.

However, in contrast with the diagnostic uses, the therapeutic uses of ultrasound such as hyperthermia and non-invasive surgery have seen relatively little progress due to several technological barriers.

The primary impediment has been a lack of the ability to monitor temperature in the treatment region during the therapeutic treatment process.

Specifically, one of objectives of the therapeutic application is to create a very well-placed thermal gradient in the target tissue to selectively destroy certain regions thereof. For example, hyperthermia technique typically requires to maintain the tissue temperature near about 43 degrees Celsius, while the goal of non-invasive surgery is typically to elevate the tissue temperature above and beyond about 55 degrees Celsius. Moreover, during the therapeutic treatment process, the physiological response of the target tissue is directly related to the spatial extent and temporal duration of the heating pattern. Consequently, in order to appropriately perform feedback and control of the therapeutic treatment process for obtaining successful results, it is absolutely essential to monitor the temperature in the target tissue, for example, so as to know whether or not the temperature in the treatment region has been raised to a level that produces a desired therapeutic effect or destruction in the tissue. In addition, it is preferable to know the temperature distribution in the treatment region and the vicinity thereof for enhancing the therapeutic effect.

In the conventional technique, the therapeutic ultrasonic system has typically relied upon thermocouple probes for monitoring the temperature in the treatment region and the vicinity thereof. However, the thermocouple probes are highly invasive because they have to be inserted into the region-of-interest. In addition, use of the thermocouple probes has necessarily led to very poor spatial resolution since only a small number of probes could be safely embedded in the region-of-interest. Furthermore, the thus embedded thermocouple probes are likely to disturb the acoustic propagation in the tissue and typically cause excessive heating at the probe interface during the therapeutic treatment process. This results in undesirably modified temperature distribution as well as erroneous measurements.

Another factor which has curtailed progress in the therapeutic uses of ultrasound has been the design of the conventional acoustic transducers.

In general, for the therapeutic treatment process, imaging of the treatment region is necessary to determine the location of the treatment region with respect to the acoustic transducers as well as to evaluate progress of the treatment process. Such essential functions of imaging as well as the aforementioned temperature monitoring may be implemented with the same acoustic transducer to be used for the therapeutic purposes, since the acoustic transducers can actually produce an image of the region-of-interest by employing well-established imaging technique such as B-scan imaging. However, the conventional acoustic transducers which are typically employed for the therapeutic purposes are acoustically large, often single-element devices having narrow bandwidth in the frequency domain. Although they are designed to efficiently transmit acoustic energy to the target tissue, the conventional acoustic transducers are typically unsuited for imaging of the treatment region and/or monitoring the temperature profile therein. This precludes development and implementation of these vital functions for performing a desirable precise therapeutic treatment process.

Some prior art references teach the use of ultrasound for therapeutic purposes. For example, U.S. Pat. No. 4,757,820 to Itoh discloses an ultrasound therapy system having functions of imaging and heating the target using ultrasound beams for the therapeutic purposes. The system disclosed therein, however, does not have the temperature monitoring function.

U.S. Pat. No. 5,370,121 to Reichenberger et al. discloses a method and an apparatus for non-invasive measurement of a temperature change in a subject, in particular a living subject, using ultrasound waveforms. The method and apparatus disclosed therein, however, relies on a differential ultrasound image between two successive ultrasound images of the target. In other words, any temperature change is detected as a temperature-induced change in brightness between the two images, which appears in the differential image. Consequently, an actual real-time monitoring of the temperature may be difficult in the disclosed method and apparatus. Moreover, although the method and apparatus can detect changes in the temperature of the target, an absolute value of the target temperature may not be obtained therefrom. In addition, any movement of the target may introduce changes in the differential image, which may cause erroneous results.

Furthermore, although it is not distinctly intended to be applied in the therapeutic treatment process for the target tissue such as in the human body, U.S. Pat. No. 5,360,268 to Hayashi et al. discloses an ultrasonic temperature measuring apparatus in which a temperature of the target medium is calculated using a propagation time of ultrasonic waves which propagated for a predetermined distance in the target medium. The apparatus disclosed therein, however, is mainly described as employing separate ultrasonic elements which respectively function for a transmitter and a receiver of the ultrasonic waves.

While some prior art temperature monitoring techniques exist, see, for example, U.S. Pat. No. 4,807,633 issued to Fry on Feb. 28, 1 989, such techniques are complex and have limited applicability. That is, use of such techniques essentially preclude use of the system for purposes of imaging, unless one were to use multiple transducers. In that regard, while two or more physically separated transducers can be used to accomplish imaging and therapy, typically with one configured for imaging and the other for therapy, such a system is susceptible to the generation of imprecise data and is overly complex and expensive.

Thus, it would be advantageous to provide a compact, non-invasive system capable of acoustically performing the therapeutic heating and the imaging of the treatment region in the target tissue as well as the temperature monitoring in the treatment region with a single acoustic transducer.

SUMMARY OF THE INVENTION

In accordance with various aspects of the present invention, a non-invasive therapeutic ultrasonic system is provided, which features a single acoustic transducer and some other subsystems capable of acoustically performing therapeutic heating and imaging of the treatment region as well as acoustically monitoring the temperature profile in the treatment region and the vicinity thereof. Also disclosed herein is a system architecture and associated components as well as algorithms which can be implemented to acoustically achieve the heating, imaging, and temperature monitoring functions. The imaging and monitoring functions allow precise feedback and control of the therapeutic treatment process so that the therapy can be conducted more successfully. In addition, because a single transducer is utilized perfect correspondence is obtained; that is, image artifacts and/or imprecise registration difficulties yielded through use of multiple transducers can be avoided.

A novel acoustic transducer disclosed herein is capable of generating high acoustic power for the therapeutic treatment process, while at the same time providing a good imaging function. Specifically, in order to obtain good lateral resolution in the imaging process, the acoustic transducer of the present invention is preferably divided into an array of sub-elements, each processing acoustic waves with a sufficient bandwidth for good axial resolution in the imaging process.

These imaging requirements are also extended to the acoustic temperature monitoring function of the treatment region. In accordance with various aspects of the present invention, an acoustic temperature measurement subsystem disclosed herein is capable of non-invasively mapping the temperature distribution or profile in the target tissue in real-time. This feature is accomplished by measuring the time-of-flight and amplitude data of acoustic pulses through the region-of-interest while exploiting the temperature dependence of the speed of sound and acoustic attenuation in the target tissue. The acoustic nature of this process allows the same acoustic transducer which is used for the imaging and therapy functions to be used for the real-time temperature monitoring function. Alternatively, the use of the multiple acoustic transducers allows the temperature mapping to be conducted with a higher spatial resolution. The thus gathered valuable information on the temperature in the target tissue can be used to achieve precise control of the spatial distribution of heating, detailed knowledge of the heating duration, and quantitative temperature data during the therapeutic treatment process, which has not been previously possible in the conventional art.

BRIEF DESCRIPTION OF THE DRAWINGS FIGURES

Preferred exemplary embodiments of the present invention is described in conjunction with the appended drawing figures in which like numerals denote like elements, and.

DETAILED DESCRIPTION OF THE PREFERRED EXEMPLARY EMBODIMENTS

A system for achieving successful ultrasonic therapy procedures in accordance with the present invention includes four major subsystems or components. Specifically, they are an acoustic transducer assembly, an imaging subsystem, a therapy subsystem (also referred to as a "therapeutic heating subsystem"), and a temperature monitoring subsystem, which are illustrated in FIGS. 1 through 4, respectively. Although not shown in the drawing figures, the system further includes components typically associated with a therapy system, such as any required power sources, memory requirements, system control electronics, and the like.

Figure 1:
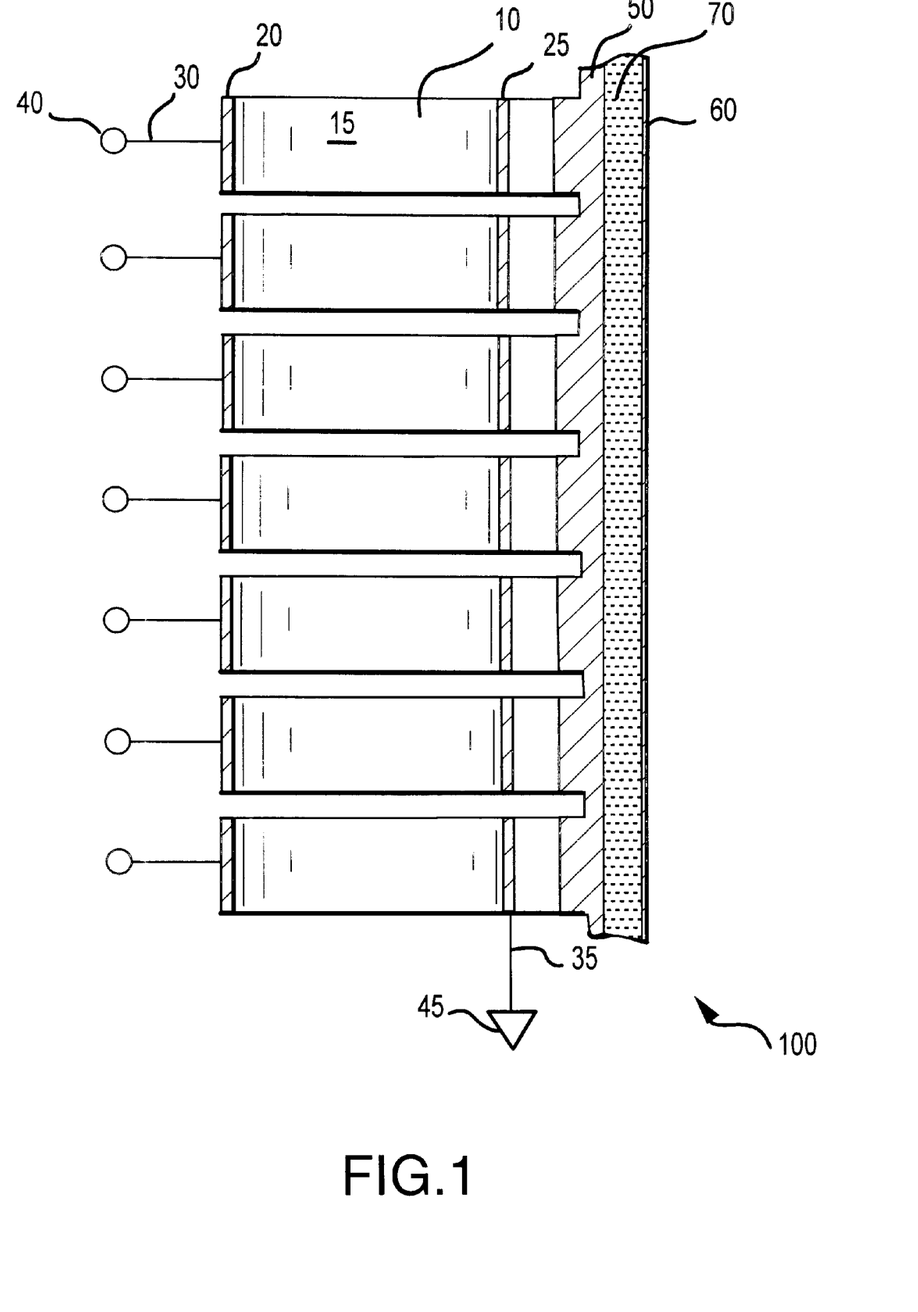
FIG. 1 is a cross-sectional view of an acoustic transducer assembly according to the present invention.

With reference to FIG. 1, the acoustic transducer assembly 100 included in the system of the present invention will be described in detail below. As shown in the cross-sectional view of FIG. 1, the acoustic transducer assembly 100 includes a piezoelectric ceramic plate 10. The air-backed side of the ceramic plate 10 is partially diced to have a plurality of curved (e.g. concave) portions 15 to form a linear array structure. The thickness of the diced ceramic plate is selected to provide a center frequency for example from 500 kHz to 20 MHz, with lower frequencies yielding deeper penetration and higher frequencies providing greater resolution. The convex portions 15 constituting the transducer array are spaced to achieve good lateral resolution in the imaging function. On the face of each of the convex portions 15, a metal electrode 20 is provided to connect the ceramic plate 10 to the system control electronics (not shown in the figure) via a cable 30 and a terminal 40. The other face of the ceramic plate 10 is configured such as to receive a common metal electrode 25. The common electrode 25 is also connected to the system control electronics via a cable 35 and a terminal 45.

The phrase "air-backed" means that there is no backing material provided on the back side of the acoustic transducer assembly 100, unlike the typical conventional acoustic transducers. Specifically, the conventional acoustic transducers are typically provided with some kinds of the backing layer typically made of a loaded epoxy, such as an alumina powder epoxy. The loaded particles in the backing layer, however, introduces increased acoustic impedance as well as providing scattering surfaces therein. Accordingly, when the generated acoustic waves come to the backing layer and hit the loaded particles included therein, the particles tend to disburse the acoustic waves in different directions into the epoxy matrix so that attenuation increases. As a result, the operational efficiency of the acoustic transducer decreases since some portion of the generated acoustic energy is absorbed in the backing layer. On the other hand, in the acoustic transducer assembly 100 of the present invention, by providing no backing layer on the back end of the ceramic plate 10, the acoustic waves are reflected without being absorbed there to propagate toward the target tissue, resulting in the increased efficiency.

Alternatively, a certain backing layer may be provided as long as it has a very low acoustic absorption so that any significant absorption of the generated acoustic energy does not happen.

On the common electrode 25, one or more acoustic matching layers 50 is bonded using an adhesive such as an epoxy. When a loaded epoxy is used as the adhesive, the acoustic matching layer 50 can be simply cast thereon since they adhere naturally to each other. The acoustic matching layer 50 is intended to obtain appropriate impedance matching between the ceramic plate 10 and the target tissue. Consequently, efficient transfer of acoustic power from the ceramic plate 10 to the target tissue can be maintained to achieve an appropriate temperature increase in the target tissue, resulting in desired therapeutic results. When the acoustic matching layer 50 (or layers) is bonded to the ceramic plate 10 (precisely, to the common electrode 25) with a loaded epoxy, the acoustic impedance can be easily adjusted by changing the amount of metal particles loaded in the epoxy.

At the same time, acoustic matching layer(s) 50 can increase the bandwidth of the emitted acoustic waves in the frequency domain. This aspect is suitable for the effective imaging function.

Specifically, in order to improve the sensitivity in the imaging function, it is preferable that the emitted acoustic waves are very pulsive in the time domain since acoustic pulses with a very short pulse width can produce clearly distinct echoes from different interfaces existing in the target tissue. The shorter the width of the acoustic pulses is, the more clearly the distinct echoes can be resolved, resulting in improved resolution in the obtained images. The short pulse in the time domain means a wide range in the frequency domain which covers a large spectrum. On the other hand, however, when considering an efficient transmission of the acoustic energy from the acoustic transducer assembly 100 to the target tissue which is important for the therapeutic treatment process, it is preferable to use stable acoustic waves such as "continuous waves" or gated bursts, which in turn means that the bandwidth thereof in the frequency domain is narrow. Thus, trade-off between the efficiency in the therapeutic function and the sensitivity in the imaging function has to be satisfied by appropriately setting the bandwidth of the acoustic waves to be emitted.

Without acoustic matching layer(s) 50, the bandwidth of the emitted acoustic waves is determined mainly based on the design of the ceramic plate 10 which actually generates the acoustic waves. This results in the limited degrees of freedom for adjusting the bandwidth. Providing one or more acoustic matching layer(s) 50 makes it possible to properly adjust the bandwidth in a wide range without substantially changing the design of the ceramic plate 10.

Typically, the thickness of the acoustic matching layer 50 is set to be on the order of a quarter of a wavelength of the acoustic waves. In addition, it is preferable that the acoustic impedance of the acoustic matching layer 50 be set to be approximately equal to the square root of the acoustic impedance of the ceramic plate 10 times the acoustic impedance of the target tissue or, more preferably, the acoustic impedance of the ceramic plate raised to the $\frac{1}{3}$ power, times the acoustic impedance of the target tissue raised to the $\frac{2}{3}$ power. Also, multiple matching layers may be used, of course, with suitable changes in layer impedances.

The acoustic matching layer 50 can be made of various types of materials, such as ceramics, plastics, metals and a composite material thereof. Preferably the matching layer may exhibit good thermal conductivity and low acoustic attenuation. Matching layer (or layers) 50 may be cut or diced, such as shown on FIG. 1, to maintain high acoustic isolation, i.e., low acoustic crosstalk. However, any heating of the matching layer(s) of ceramic may be controlled via the duty cycle of the drive signal or via active or passive cooling methodologies. In addition, any other conventional cooling technique and/or methodology may be utilized.

Although not shown on FIG. 1, it should be appreciated that transducer assembly 100 may be provided with a back layer (not shown) suitably configured to modify the bandwidth of the transducer and/or serve as a heat sink.

The ceramic plate 10 and other related components configured as set forth above are coupled to the target tissue via a fluid 70 circulating between the acoustic matching layer 50 and an acoustically-transparent membrane 60. The fluid 70 also functions as a coolant for the ceramic plate 10 and the acoustic matching layer 50 and may also aid in controlling the temperature of the tissue at the interface. Temperature control via a circulating fluid, thermoelectric cooling module and/or pneumatic or other devices may also be utilized in accordance with various aspects of the present invention. Furthermore, the acoustic transducer assembly 100 having the aforementioned configuration is enclosed in a water-tight housing (not shown in the figure).

The circulating fluid 70 has two major functions as mentioned above. One of them is to couple the ceramic plate 10 and the acoustic matching layer 50 to the target tissue.

The other is to remove the waste heat away from the acoustic transducer assembly 100. In particular, the energy conversion efficiency of the acoustic transducer assembly 100 is typically about 80%, and consequently, some portion of the input electrical power becomes the waste heat. When a large amount of electrical power is input to the acoustic transducer assembly 100, the assembly 100 is heated up. This may result in reduced efficiency and altered operational characteristics, which are likely to produce adverse effects on the therapeutic purposes. The circulating fluid 70 therefore keeps the acoustic transducer assembly 100 at a stable and constant temperature by cooling it off.

The fluid 70 is typically water. Alternatively, any suitable mineral oil, plant oil, or other suitable liquid could be used as the fluid 70.

Figure 2:
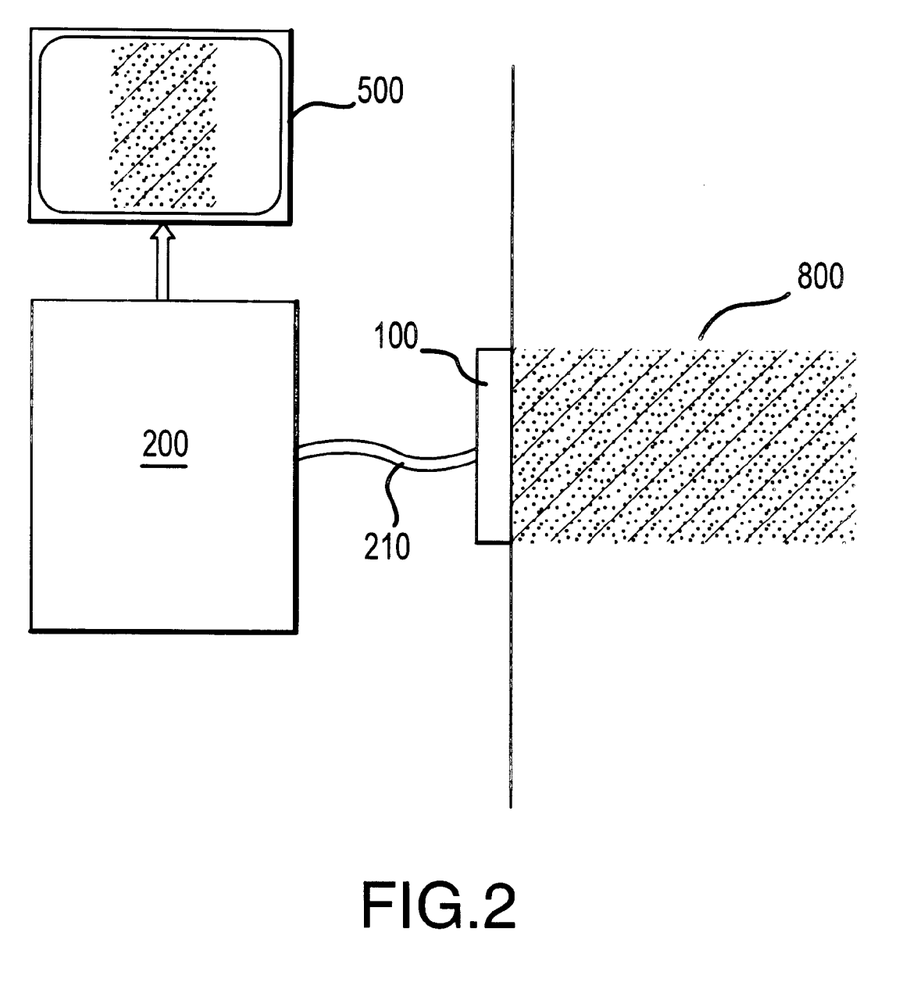
FIG. 2 is a diagram of an imaging subsystem interfaced to the acoustic transducer assembly according to the present invention.

With reference to FIG. 2, an imaging subsystem 200 which is interfaced to the acoustic transducer assembly 100 is described below. The imaging subsystem 200 connected to the acoustic transducer assembly 100 via a cable 210 includes a beam forming control unit. The unit is operated so that the acoustic transducer assembly 100 scans the region-of-interest, including the treatment region, in the target tissue 800 with the acoustic waves. The returning acoustic signal is received by the acoustic transducer assembly 100, and then sent to the imaging subsystem 200 to generate ultrasonic images of the treatment region. The thus generated image is displayed on a video display terminal 500 to assist the user in appropriately positioning the acoustic transducer assembly 100 with respect to the treatment region in the target tissue 800 prior to actually commencing the therapeutic treatment process.

Figure 3:
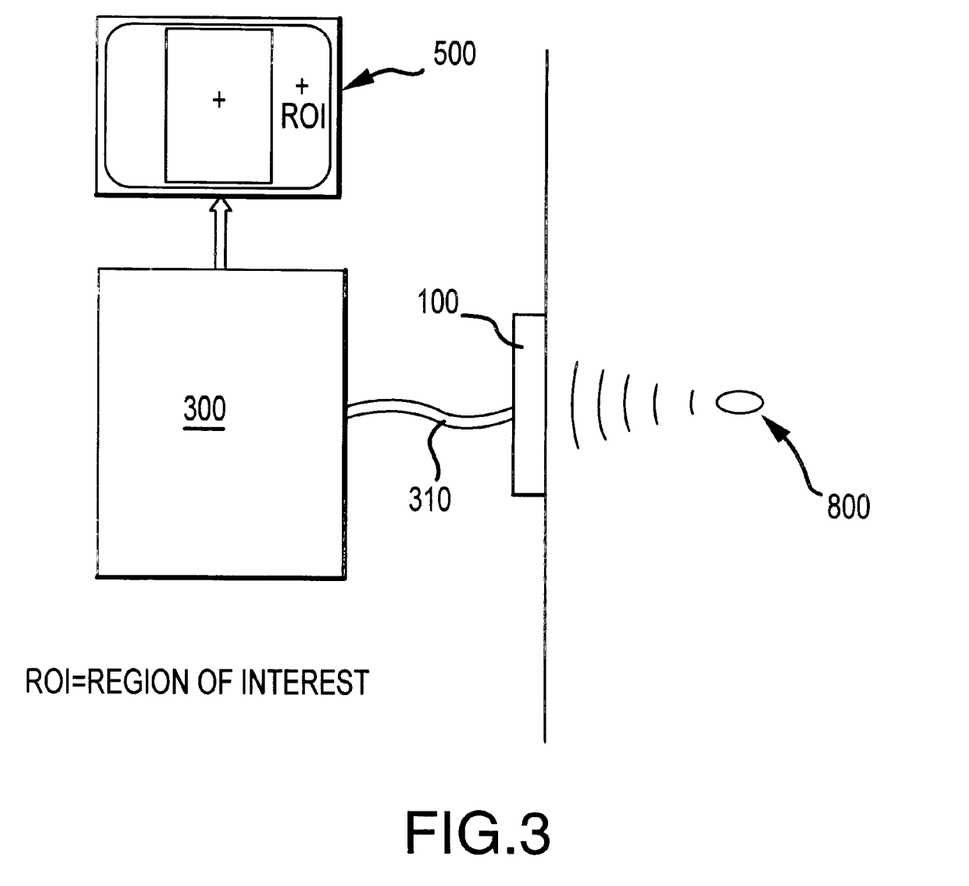
FIG. 3 is a diagram of a therapy subsystem interfaced to the acoustic transducer assembly according to the present invention.

With reference to FIG. 3, a therapy subsystem (a therapeutic heating system) 300 which is interfaced to the acoustic transducer assembly 100 is described below.

The therapy subsystem 300 connected to the acoustic transducer assembly 100 via a cable 310 includes power RF drivers which are interfaced to the linear array of the acoustic transducer assembly 100, i.e., to each of the respective portions 15 of the ceramic plate 10 shown in FIG. 1. The power RF drivers are also connected to the common electrode 25 provided on the other face of the ceramic plate 10. By appropriately applying RF signal voltages to the ceramic plate 10 from the thus connected power RF drivers, high power acoustic energy is generated. The drivers are controlled in-time so that the acoustic transducer assembly 100 transmits, steers, and/or focuses the acoustic waves to the region-of-interest including the treatment region in the target tissue 800. Heating power and heating time as well as transducer anodization are all controlled during the therapeutic treatment process to achieve the proper heating pattern and therapeutic dosage. The control can be supplemented by the feedback of information from the temperature monitoring subsystem described later.

In connection with yet another embodiment of the present invention, temperatures are monitored in a manner calculated to avoid tissue motion artifacts. For example, in the case where a localized region is heated, in accordance with this embodiment of the present invention, the heated region is interrogated with a pulse echo signal substantially immediately thereafter. In such a case the echo from the heated region will be changed in time and amplitude. For example, the acoustic attenuation in tissue approximately doubles from 50° C. to 70° C. Preferably, the region is measured immediately before and after heating and thus, tissue motion artifacts are avoided, as well as any acoustic propagation effects.

In the case where only a small region is treated at a time, an isothermal region about the hot spot is engendered. Therefore, the time-of-flight and the amplitude of wave incident on the heated region is the same before and after the therapeutic energy is delivered. Thus, the amplitude change and time change measured after therapy will be due substantially to the tissue treated.

Figure 4:
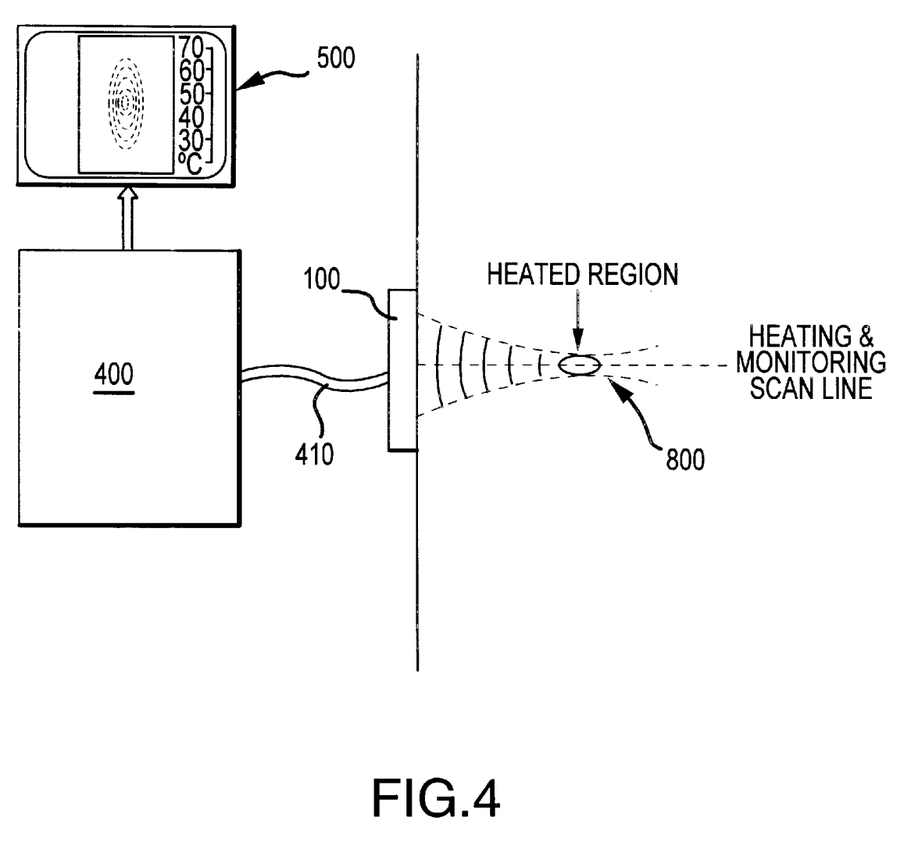
FIG. 4 is a diagram illustrating a temperature monitoring subsystem according to the present invention.

With reference to FIG. 4, a general schematic utilizing this approach is shown where transducer assembly 100 is used to heat a small region 800. As shown, the temperature monitoring subsystem 400 is connected to display 500. Temperature monitoring subsystem 400 is also connected to transducer assembly 100, such as by a suitable cable 410. In accordance with this aspect of the present invention, the whole volume is scanned, and by sweeping the pulse echo the effective thermal dose (time/temperature history) (e.g. recrossed volume) can be determined. In the context of the present invention the term thermal dose relates to the temperature and time of duration integral function by which, for example, a determination of necrosity can be made.

Figure 5:
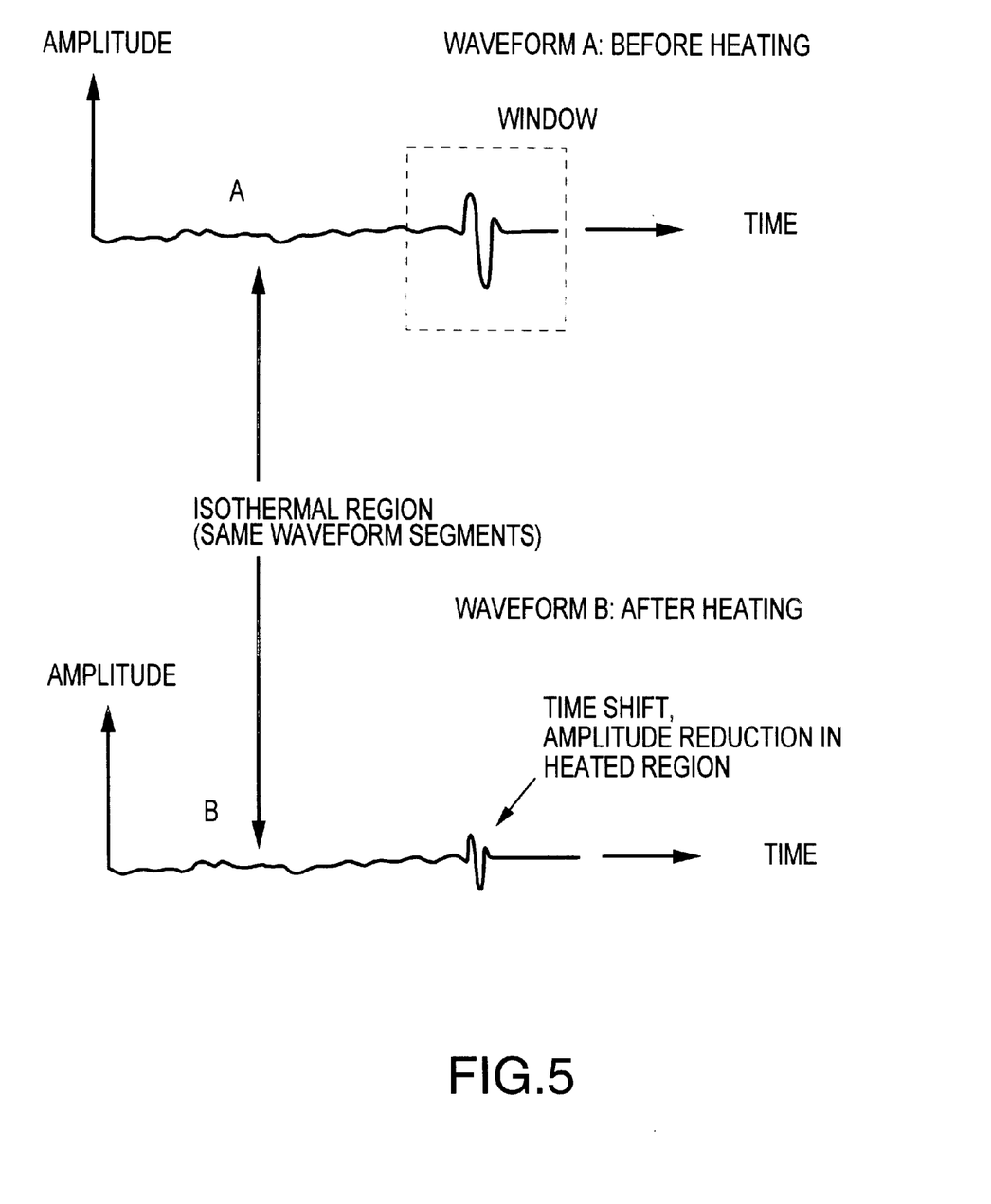
FIG. 5 depicts waveforms of heated and unheated states illustrating the time shift and amplitude change of the echo in the region of interest.

With reference to FIG. 5, the echo waveform in a windowed region of a waveform A obtained before heating and a waveform B after heating can be examined, and based on the time-duration and spatial extent of the heated area, i.e. the time shift of the echo in the heated region and tissue and thermal properties, the temperature can be determined.

Alternatively, instead of evaluating the time shift, the echo amplitude in the windowed region could be examined. In accordance with this aspect of this embodiment of the present invention, when the amplitude of the signal in the windowed region begins to rapidly fall, the temperature will be in the 50° C. to 70° C. range. In this manner the effective necrosed volume can be determined.

It should be appreciated that in accordance with various aspects of the present invention, both echo time shifts and amplitude changes may be employed. For example, by scanning the windowed region in one, two, or three dimensions, a temperature map or image can be obtained.

Of course this technique may also be performed on an incremental basis to compensate for changes in temperature along some line, including, for example, before/after the hot spot. For example, by windowing out regions from the transducer to the region of interest and in each region computing the temperature from attenuation techniques or phase shifts, a temperature profile can be accurately determined.

Figure 6:
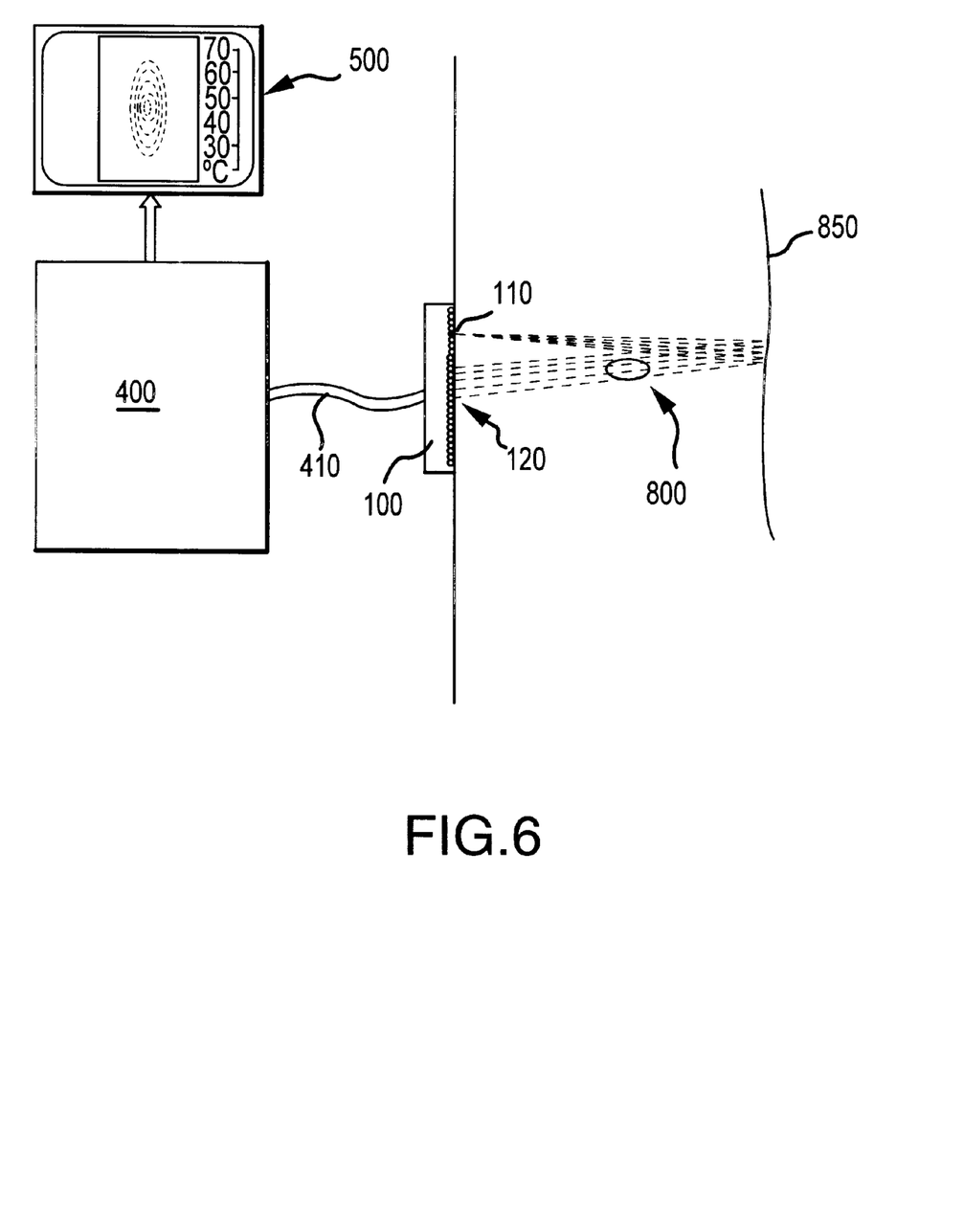
FIG. 6 is a diagram of a further embodiment of a temperature monitoring subsystem interfaced to the acoustic transducer assembly according to the present invention.

With reference to FIG. 6, a temperature monitoring subsystem 400 which is interfaced to the acoustic transducer assembly 100 and monitor 500 is described below. The temperature monitoring subsystem 400 connected to the acoustic transducer assembly 100 via a cable 410 includes a control unit. The unit is operated so that the temperature mapping process as follows is properly conducted.

In particular, an acoustic pulse wave is first generated by a single transmitting element 110 among the linear array of the acoustic transducer assembly 100. The thus generated acoustic pulse wave propagates into the target tissue 800 and through any temperature gradients. Since the speed of sound in the target tissue 800 exhibits temperature dependency, the acoustic wavefronts will be sped up or slowed down in certain regions based on the temperature gradients existing in the target tissue 800. Upon reaching a boundary 850 used for reference, the acoustic wavefronts are reflected thereon so that the reflected wavefronts, i.e., the echoes come back towards the acoustic transducer assembly 100, where they are detected by remaining elements 120 in the linear array.

Upon the echoes returned from the target tissue 800 are detected by the acoustic transducer assembly 100, a certain signal is sent to the temperature monitoring subsystem 400 in which the time-of-flight data of the detected echoes (ire., the returned acoustic wavefronts) which is a period of time required from the emission of a certain acoustic pulse to the detection of the corresponding echo (the reflected acoustic wave) is calculated. The above transmitting-and-detecting sequence is repeated for each unique transmitter-receiver combination to form a large data set.

Finally, using propagation path data, the obtained time-of-flight data is numerically converted into speed data of sound in the target tissue, and then further into a matrix of temperature values. Specifically, the speed V of sound (in this case, the speed of the ultrasonic wave) in the target tissue is expressed as follows:

$$V=Vo+f(T) \quad (1)$$

where Vo represents the speed of sound at a certain temperature in the target tissue, T is a temperature of the target tissue, and f(T) is a function of T. Furthermore, the speed V of sound is also expressed as follows:

$$V=L/t \quad (2)$$

where L represents the length of the propagation path while t represents the propagation time (i.e., the time of flight) which is required for the sound (i.e., the acoustic wave) to cover the propagation path of the length L.

As a result, from the above-mentioned expressions (1) and (2), the temperature T of the target tissue can be calculated based on the measured time-of-flight (the propagation time) data t with using values for L, Vo and f(T). Typical values for Vo and f(T) are known in the art or readily measured in experiments. On the other hand, the propagation path length L for the above calculation can be determined in several manners.

For example, a small biopsy needle, typically metallic, with a square cross-section can be placed in the target tissue until reaching a predetermined depth. Such a metallic needle provides a large amount of reflection of the acoustic waves, thereby functioning an artificial reference boundary placed at the predetermined known depth in the target tissue.

Alternatively, instead of providing the artificial boundary, any natural boundaries existing in the target tissue can be used as the reference boundary which provides the basis of calculating the propagation path length. Such natural boundary will include a tissue-to-air boundary, a tissue-to-water boundary, a tissue-to-bone boundary, and the like.

When any actual artificial or natural boundaries are not available in the target tissue as the reference boundary, an imaginary boundary or a virtual boundary can be produced. When one acoustic pulse or wave is emitted toward the target tissue at a time of zero (0) and the corresponding returning echo is detected at a time of X, then the specific pulse or wave has traveled in the target tissue over a distance which is approximately calculated as X times the speed of sound. Thus, the signal processing and analysis in the subsequent processes can be conducted based on this particular echo as the reference.

Analogous to the time-of-flight data, and use thereof as described herein, in accordance with various aspects of the present invention, the amplitude of the returned echos can also be used to create an image of the acoustic attenuation.

The obtained temperature data is sent to the video display terminal 500 for visualization by the user, and also sent to the therapy subsystem 300 previously described for dynamic control of the heating process for the therapeutic treatment purposes.

Figure 7:
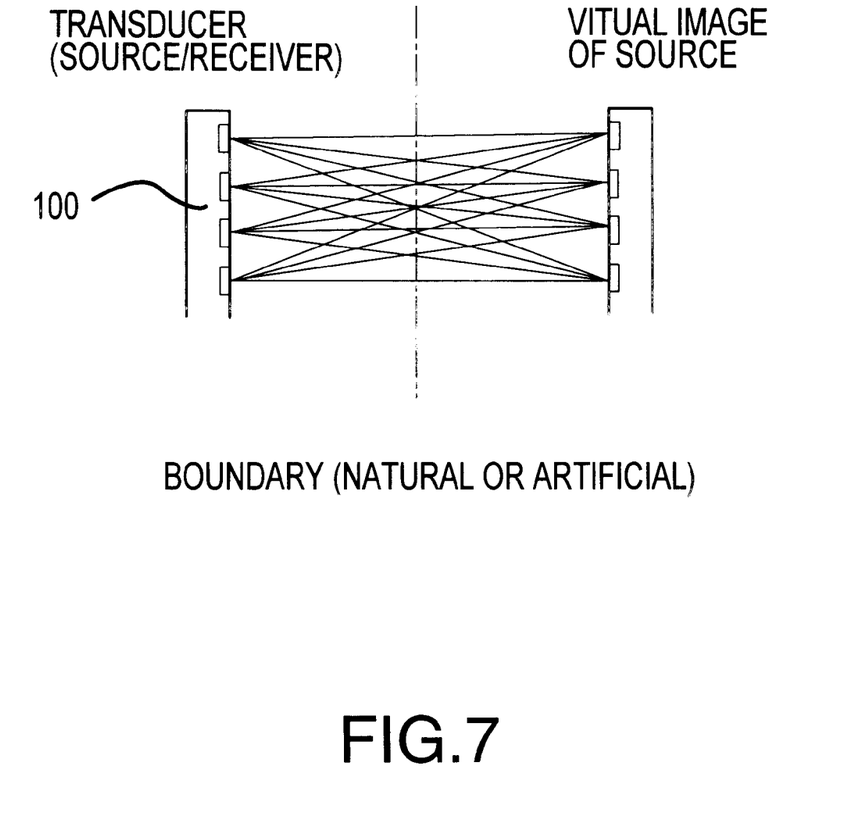
FIG. 7 is a depiction of the intersecting paths of acoustic rays possible from a transducer source.

In accordance with yet another embodiment of the present invention, temperature can be monitored using a tomographic approach (in addition to FIG. 6 embodiment). With reference to FIG. 7 the intersecting path of a transducer 100 having multiple elements is illustrated. The path of propagation is determined by the diffraction of the source and the properties of the medium. Along a path s the acoustic time-of-flight, τ will be the integral of the incremental delays over s $$\tau = \int \frac{ds}{v(s)} \quad (3)$$

It should be appreciated that the acoustic propagation will consist of phase retardation (additional delay) and diffraction loss (amplitude loss), refraction, and various tissues with associated speed of sound characteristics, and each of these factors can, if desired, be included in the analysis.

Figure 8:
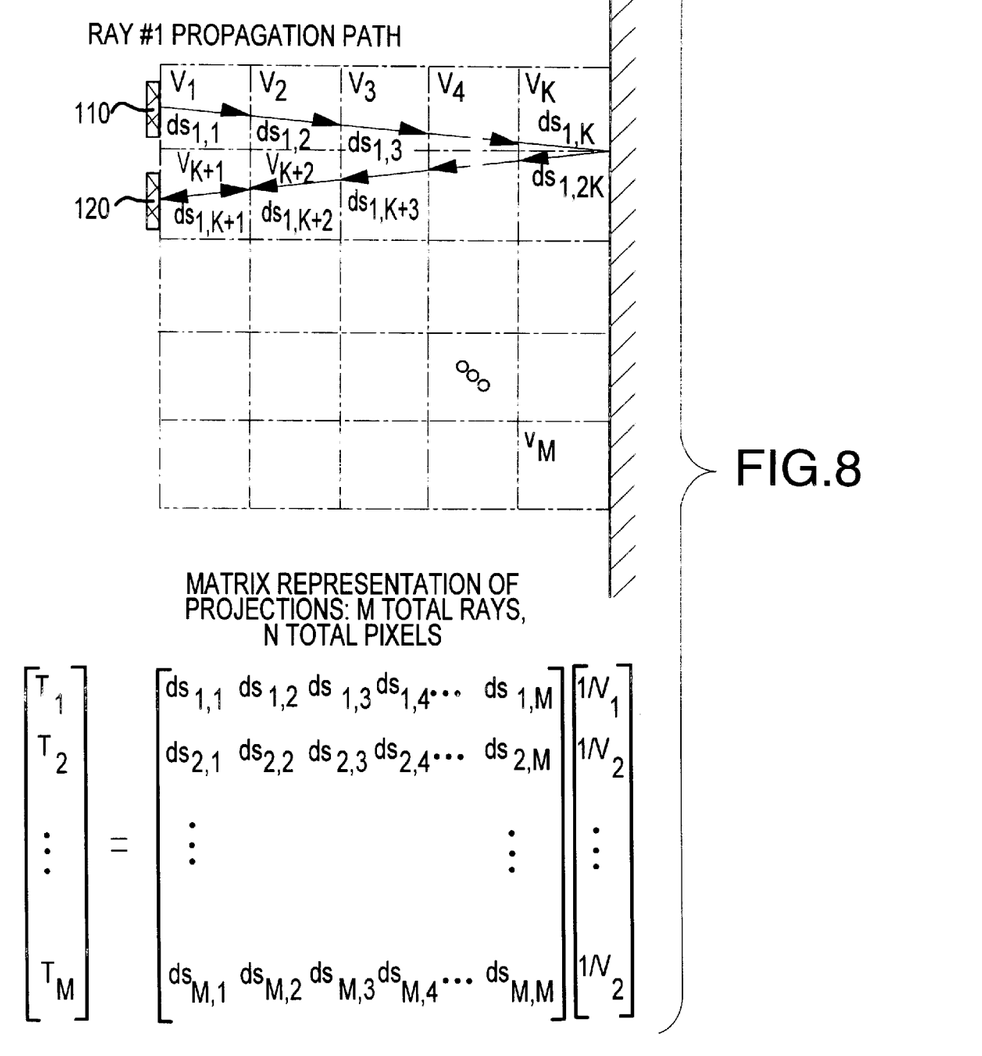
FIG. 8 illustrates a tomographic configuration useful in connection with yet another embodiment of a temperature monitoring subsystem according to the present invention.

In any event, by considering the intersecting paths, such as shown in FIG. 7, superimposed over a grid of pixels, where each pixel represents an area (volume) a tomographic configuration shown in FIG. 8 is obtained. By tracing the propagation and reception of the rays a solution to the velocity in each pixel from the matrix can be calculated according to the following equation:

$$[\tau] = [ds]\left[\frac{1}{v}\right] \quad (4)$$

where [τ] is a vector of measured delays, [ds] a matrix of known distances and [1/v] a vector of slowness, the reciprocal of the speed of sound (and thus temperature) in each pixel. Given the dependence of the speed of sound in tissue with temperature, the spatial temperature distribution in each pixel is thus determined. As noted briefly above, other factors including acoustic diffraction (beam spreading) and the temperature coefficients of tissue can be incorporated to enhance the accuracy of this method. In accordance with a particularly preferred aspect, the array can be rotated to allow for a three-dimensional map of temperature to be measured.

By measuring the ray paths and then heating the region and rapidly remeasuring an accurate spatial map of heating is obtainable, such map being substantially free of tissue motion artifacts.

As described above, the ultrasonic therapy system of the present invention includes an acoustic transducer assembly (in other words, the acoustic transducer subsystem), a therapy subsystem (in other words, a therapeutic heating subsystem), and a temperature monitoring subsystem as well as an appropriate display and control interface. This architecture non-invasively provides essential functions of real-time imaging and temperature monitoring of the treatment region during the therapeutic treatment process. This enables the user to obtain the feedback of the results of the therapeutic treatment process, resulting in improved control of the process. By using the disclosed system of the present invention, safe, automated, and well-controlled procedures for the therapeutic treatment process are achievable at low cost and in only seconds or minutes of therapy. The use of the disclosed transducer capable of imaging, therapy, and monitoring allows precise geometric placement and monitoring of lesions, which has not previously been possible with prior art systems and/or methodologies.

With reference to FIGS. 9A–D and 10A–B, the performance of a transducer made in accordance with the present invention will now be described. Specifically, a 5×5 mm therapy transducer has been constructed in accordance with the present invention and the characteristics of that transducer determined.

Figure 9A:
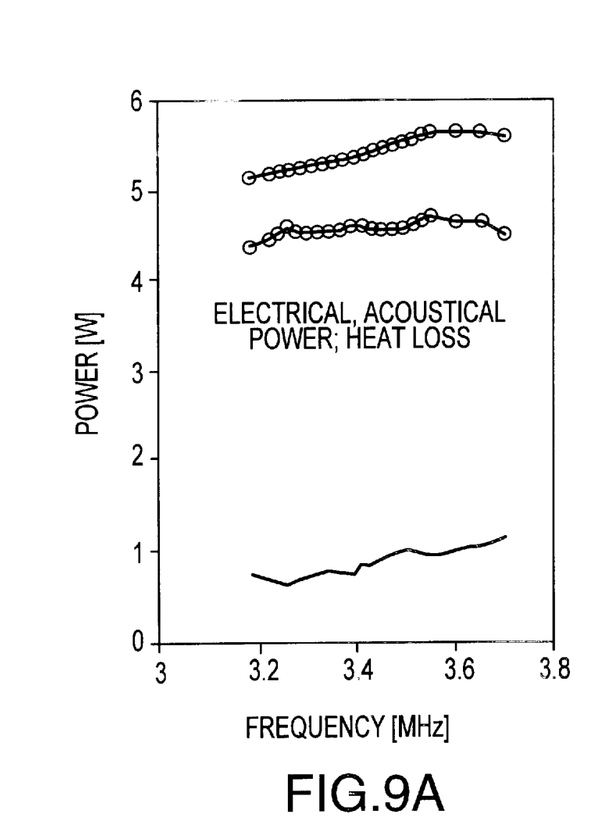
FIGS. 9A–D show the characteristics of an exemplary transducer made in accordance with various aspects of the present invention.
Figure 9B:
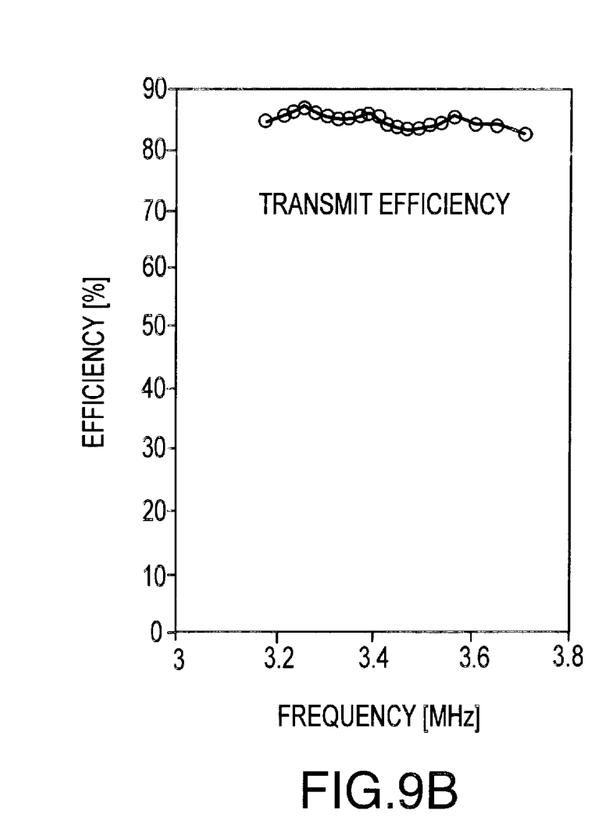

With respect to FIG. 9A, for example, the power versus frequency, respectively, plot shown therein shows the electrical input, acoustical output and heat loss. As will be appreciated, each of these aspects are well within desirable ranges. Similarly, and with reference now to FIG. 9B, the transmit efficiency of the transducer over the range of 3–4 MHz is on the order of above 80%, which, as will be appreciated by those skilled in the art, are more than acceptable. It should be appreciated that any suitable frequency range could be utilized.

Figure 9C:
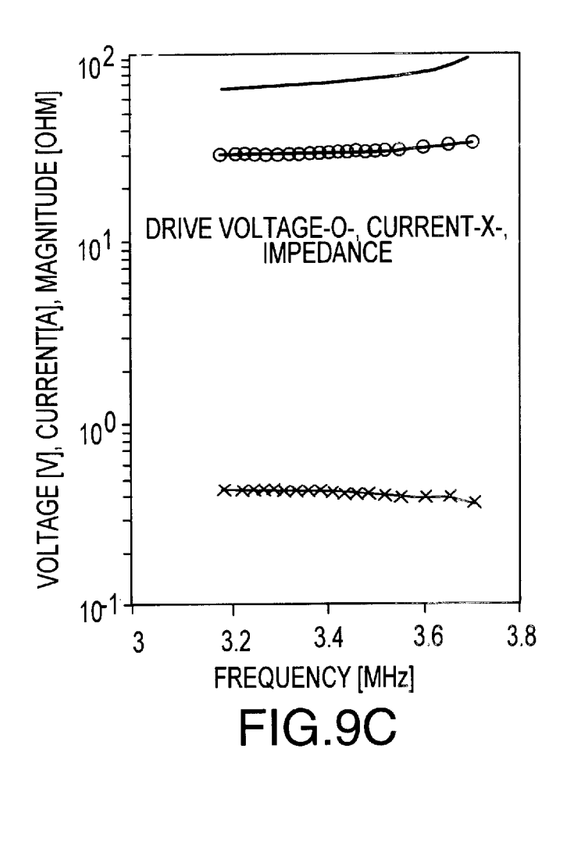

Referring now to FIG. 9C, the voltage, current and impedance magnitude of the transducer over a similar frequency range (e.g., 3–4 MHz) is shown. In accordance with this particular embodiment, the drive voltage is on the order of about 30 volts, the current on the order of about 400 milliamps, and the impedance magnitude on the order of about 70 ohms.

Figure 9D:
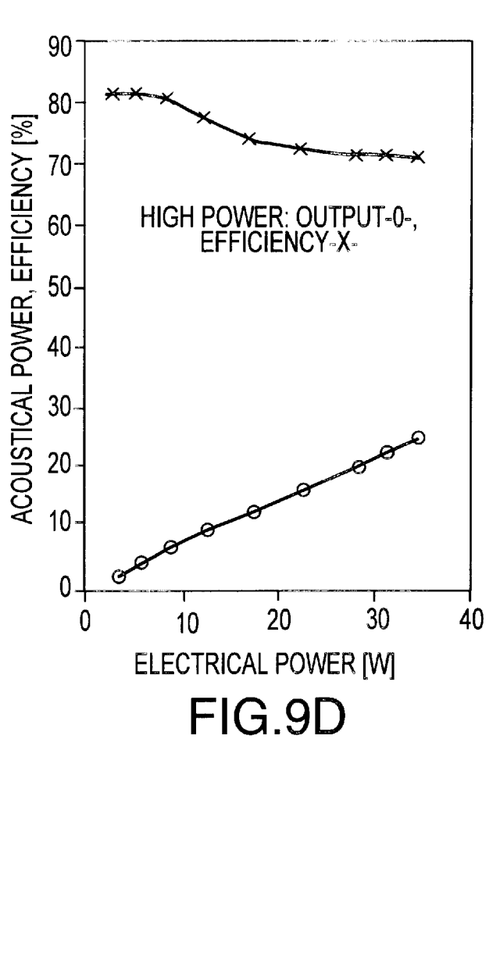

Finally, with respect to FIG. 9D, the acoustical power at high power outputs is shown, and, as such, it can be seen that as electrical power is increased, the heating efficiency drops but that over acceptable ranges transducers made in accordance with the present invention exhibit acceptable performance.

Figure 10A:
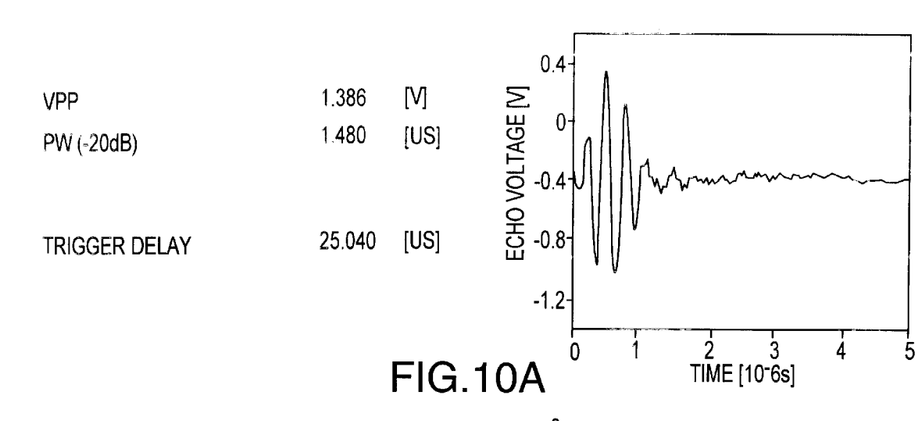
FIGS. 10A–B show, respectively, the pulse echo waveform and the frequency spectrum of the echo of an exemplary transducer made in accordance with various aspects of the present invention.
Figure 10B:
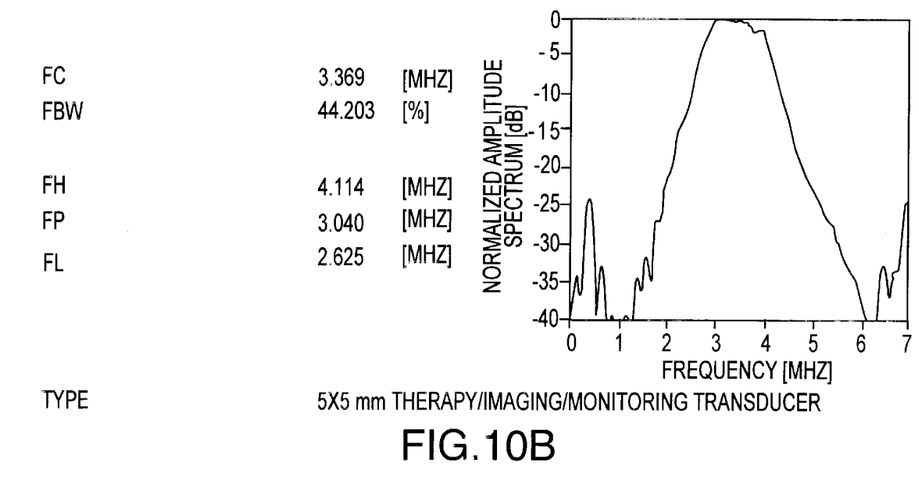

Referring now to FIG. 10, the pulse echo waveform of the aforementioned exemplary transducer is shown in FIG. 10A and the frequency spectrum of the echo, without electrical tuning, is shown in FIG. 10B. As will be appreciated by those skilled in the art, the frequency spectrum and echo voltage plots evidence the usability and functioning of transducers made in accordance with the present invention. Specifically, it will be noted that the transducers exhibit high fractional bandwidth. Although the specific transducer used in gathering the data shown in FIG. 10 comprises a transducer with a single matching layer and no electrical tuning, providing two or more matching layers, as noted above, and electrically tuning the transducer may enhance such characteristics to over 50% or more.

It will be appreciated that the invention described herein offers various advantages over the prior art techniques. However, the various embodiments were chosen and described in order to explain the principles of the invention and its practical application to enable others of ordinary skill in the art to best utilize the invention in various embodiments and with various modifications as are suited to the particular use contemplated. It is intended that the scope of the invention be defined by the claims attached hereto.

We claim:

1. A combined imaging, therapy and temperature monitoring system comprising:

a single acoustic transducer comprising an array of sub-elements, said transducer which produces an ultrasonic signal for ultrasonic imaging of a target tissue on a display;

said transducer also for producing an ultrasonic signal for temperature measurement by creating a map of the temperature distribution in said target tissue on said display and;

said transducer adapted to provide controlled heating of said target tissue.

2. An ultrasound system comprising:

an acoustic transducer assembly comprising a single transducer, said single transducer producing signals including an imaging signal, a therapy signal, and a temperature signal, said single transducer enabling the ultrasound system to perform substantially simultaneously imaging, therapy, and temperature monitoring; and a display;

wherein said imaging signal generates an image of a treatment region on said display, said therapy signal generates high power acoustic energy to heat said treatment region, and said temperature signal generates a map to monitor the temperature of said treatment region and display the same on said display.

3. The system of claim 2, wherein said acoustic transducer assembly comprises an air-backed piezoelectric ceramic array.

4. The system of claim 3, wherein said acoustic transducer assembly further comprises an acoustic matching layer suitably attached to said transducer assembly such that an efficient transfer of acoustic power from said ceramic array to said treatment region can be maintained.

5. The system of claim 4, wherein said acoustic transducer includes more than one acoustic matching layer.

6. The system of claim 3, wherein said ultrasound system further comprises a beam forming control unit to interface with said acoustic transducer assembly such that said acoustic transducer assembly scans a region-of-interest, including a treatment region, in said target tissue with acoustic waves, the returning acoustic signal being received by said acoustic transducer assembly, and then ultrasonic images of said treatment region are generated for display on said display.

7. The system of claim 6, wherein said ultrasound system includes power RF drivers which are interfaced to said ceramic array of said acoustic transducer assembly such that by appropriately applying RF signal voltages to said ceramic array high power acoustic energy is generated to heat said treatment region.

8. The system of claim 7, wherein said ultrasound system includes a temperature monitoring control unit to topographically evaluate the acoustic propagation of the acoustic rays from a plurality of said array elements.

9. The system of claim 8, wherein said single transducer assembly includes a plurality of n elements, and each of said n elements generates a pixel map of said treatment region, and wherein said temperature monitoring control unit manipulates data relative to the propagation and reception of the acoustic rays from each of said n elements such as to determine the spatial temperature distribution in each pixel of said pixel map.

10. The system of claim 9, wherein said single transducer is rotatably connected to said ultrasound system to allow for a three-dimensional map of temperature to be measured and displayed on said display.

11. The system of claim 9, wherein said single transducer is provided as a multiple dimensional array and allows for a three-dimensional map of temperature to be determined.

12. The system of claim 2, wherein said temperature signal is caused to interrogate the treatment region with a pulse echo signal substantially immediately after heating of said treatment region by said heating signal.

13. The system of claim 12 wherein said ultrasound system uses data reflective of the time-of-flight of said pulse echo signal and data reflective of the amplitude of said pulse echo signal to determine the temperature of said treatment region.

14. A method for therapeutic treatment comprising the steps of:

providing an ultrasonic therapy system including a single acoustic transducer, which said single transducer is included as a part of an imaging subsystem, part of a therapy subsystem, and part of a temperature monitoring subsystem, said ultrasonic therapy system further including a display, and a control interface;

generating an image of a treatment region on said display with said imaging subsystem;

generating high power acoustic energy to heat said treatment region with said therapy subsystem;

monitoring the temperature of said treatment region with said temperature monitoring subsystem; and operating said control interface to control said single transducer to non-invasively provide real-time imaging, therapeutic heating and temperature monitoring of said treatment region during the therapeutic treatment process, such that said real-time imaging, therapeutic heating and temperature monitoring are conducted through the use of said single transducer.

15. The method of claim 14, further comprising the steps of:

displaying said temperature of said treatment region on said display; and controlling the temperature of said treatment region during said therapeutic treatment process by using said real-time imaging and said temperature monitoring to provide feedback control to said control interface.

16. An ultrasound system comprising:

a display;

an imaging subsystem including an acoustic transducer assembly for generating an image of a treatment region on said display;

a therapy subsystem including said acoustic transducer assembly for generating high power acoustic energy to heat said treatment region;

a temperature monitoring subsystem including said acoustic transducer assembly for mapping and monitoring the temperature of said treatment region and displaying the temperature of said treatment region on said display; and wherein said acoustic transducer assembly comprises a single transducer such that the imaging, therapeutic heating and temperature monitoring of said treatment region are conducted substantially simultaneously through the use of said single transducer.

17. An acoustic transducer assembly for providing imaging, therapy and temperature monitoring, said acoustic transducer assembly comprising:

a single transducer operatively connected to an imaging subsystem, a therapy subsystem and a temperature monitoring subsystem such that when so connected the imaging subsystem generates an image of a treatment region on a display, the therapy subsystem generates high power acoustic energy to heat the treatment region, and the temperature monitoring subsystem maps and monitors the temperature of the treatment region and displays the temperature on a display, all through the use of said single transducer.

18. The acoustic transducer assembly of claim 17, wherein said single transducer allows the imaging subsystem, the therapy subsystem and the temperature monitoring subsystem, to operate through said single transducer in a substantially simultaneous manner.

19. An acoustic transducer assembly of claim 18, said assembly further comprising a plurality of n elements, and each of said n elements generates a pixel map of the treatment region, and wherein the temperature monitoring subsystem manipulates data relative to the propagation and reception of the acoustic rays from each of said n elements such as to determine the spatial temperature distribution in each pixel of said pixel map.

* * * * *